(12) United States Patent
Greenhut et al.

(10) Patent No.: US 8,380,295 B2
(45) Date of Patent: Feb. 19, 2013

(54) DETECTION OF WAVEFORM ARTIFACT

(75) Inventors: Saul E. Greenhut, Aurora, CO (US);
Mustafa Karamanoglu, Fridley, MN (US); Karen J. Kleckner, New Brighton, MN (US); Tommy D. Bennett, Shoreview, MN (US); Scott W. Davie, Beaconsfield (CA)

(73) Assignee: Medtronic, Inc., Minneapolis, MN (US)

( * ) Notice: Subject to any disclaimer, the term of this patent is extended or adjusted under 35 U.S.C. 154(b) by 679 days.

(21) Appl. No.: 12/609,455

(22) Filed: Oct. 30, 2009

(65) Prior Publication Data
US 2011/0105927 A1    May 5, 2011

(51) Int. Cl.
*A61B 5/04* (2006.01)
(52) U.S. Cl. .................................... 600/544; 600/300
(58) Field of Classification Search .............. 600/513, 600/544, 545, 508, 515
See application file for complete search history.

(56) References Cited

U.S. PATENT DOCUMENTS

| | | | |
|---|---|---|---|
| 3,885,551 A | 5/1975 | Massie | |
| 4,777,959 A | 10/1988 | Wallach | |
| 5,273,049 A * | 12/1993 | Steinhaus et al. | 600/508 |
| 5,297,556 A | 3/1994 | Shankar | |
| 5,337,750 A | 8/1994 | Walloch | |
| 6,549,804 B1 * | 4/2003 | Osorio et al. | 600/544 |
| 7,043,293 B1 | 5/2006 | Baura | |
| 7,395,105 B2 | 7/2008 | Schmidt | |
| 2003/0052775 A1 | 3/2003 | Shambroom et al. | |
| 2003/0144700 A1 * | 7/2003 | Brown et al. | 607/14 |
| 2006/0025825 A1 | 2/2006 | Bowers | |
| 2006/0047201 A1 | 3/2006 | Eide | |
| 2006/0149146 A1 | 7/2006 | Schmidt | |
| 2007/0032706 A1 * | 2/2007 | Kamath et al. | 600/300 |
| 2008/0234594 A1 | 9/2008 | Brooks et al. | |

FOREIGN PATENT DOCUMENTS

EP    1 050 271 A2    8/2000

OTHER PUBLICATIONS (PCT/US2010/053910) PCT Notification of Transmittal of the International Search Report and the Written Opinion of the International Searching Authority.

* cited by examiner

*Primary Examiner* — Carl H. Layno
*Assistant Examiner* — Jon-Eric C. Morales
(74) *Attorney, Agent, or Firm* — Michael C. Soldner

(57) ABSTRACT

An implantable medical device system including a physiological sensor detects signal artifact in a signal waveform acquired by the sensor. Features of individual waveforms in the sensor signal are extracted. Sample waveforms are classified by expert observation into at least two classes including an artifact class. A distribution range for each of the extracted features from the sample waveforms is determined for each of the classes. Waveform classification criteria are established in response to the determined distribution ranges.

13 Claims, 9 Drawing Sheets

DETECTION OF WAVEFORM ARTIFACT

TECHNICAL FIELD

The disclosure relates generally to implantable medical devices and, in particular, to a method and apparatus for monitoring a physiological signal in a patient and detecting waveform artifact in the signal.

BACKGROUND

Implantable medical devices are available for monitoring physiological signals in a patient. For example, a patient's blood pressure signal may be monitored using a pressure sensor typically mounted along a transvenous lead and advanced to a desired monitoring location. A pressure sensor may be positioned within a ventricular or atrial chamber or along a vein or artery for monitoring for physiological events that influence the blood pressure signal or relate to the hemodynamic status of the patient. Pressure sensor signals contain artifact due to mechanical noise, such as bumping of the pressure sensor against anatomical structures, movement caused by coughing or other respiratory maneuvers, or other movement. This signal artifact may fall within the frequency range of the desired signal properties used for monitoring the patient. As such, artifact removal using conventional filtering or other signal averaging methods may not be effective in removing the artifact without losing desired signal information. Apparatus and methods are needed, therefore, for distinguishing physiological sensor signal waveforms contaminated by artifact from waveforms that do not contain artifact to allow accurate and reliable monitoring of the patient.

DETAILED DESCRIPTION

Figure 1:
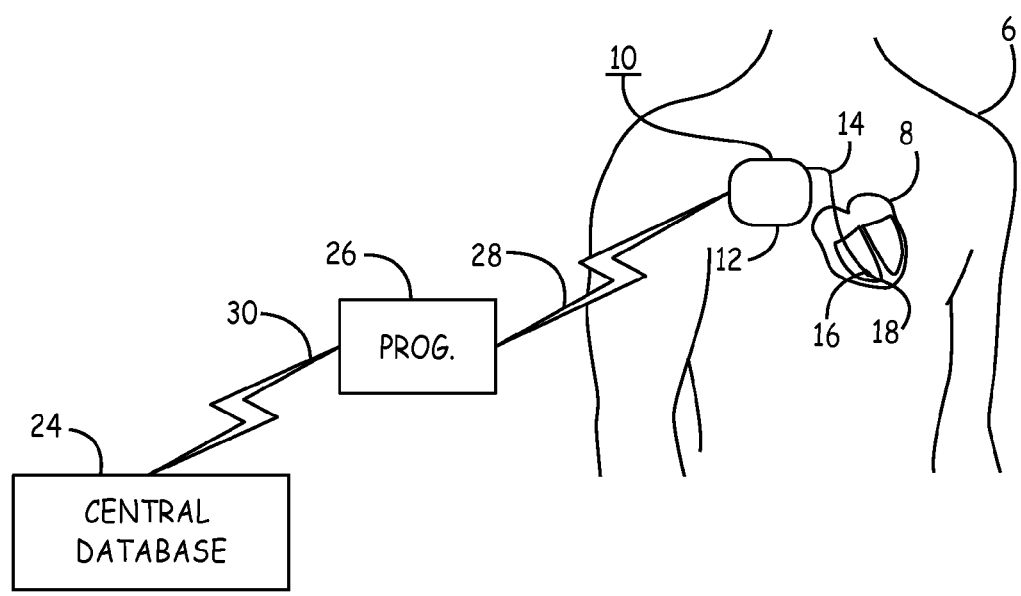
FIG. 1 is a schematic diagram of a patient monitoring system including an implantable medical device (IMD) coupled to a sensor lead positioned within a heart in a patient's body.

In the following description, references are made to illustrative embodiments. It is understood that other embodiments may be utilized without departing from the scope of the disclosure. In some instances, for purposes of clarity, for example, identical reference numbers may be used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Various embodiments described herein utilize a pressure signal acquired using a pressure sensor implantable in a patient's body for monitoring physiological events or conditions. As used herein, the term "pressure signal" includes any pressure signal measured within the body, which may include intracardiac, venous, arterial, or intra-thoracic pressures. Intracardiac pressure signals may be measured in the right or left atrium or in the right or left ventricle. In illustrative embodiments, a pressure sensor may be positioned within the right ventricle for measuring right ventricular pressure and deriving pressure monitoring metrics for monitoring a patient condition. In alternative embodiments, a pressure sensor may be positioned in the pulmonary artery for measuring pulmonary arterial pressure and deriving pressure monitoring metrics.

A pressure sensor and associated pressure signal are referred to in the illustrative embodiments disclosed herein, however, it is contemplated that the methods described may be implemented in conjunction with any physiological sensor that is subject to signal artifact. For example other sensors of mechanical phenomena, such as a motion sensor, a flow sensor, or an acoustical sensor, used to monitor a physiological signal may be subjected to similar types of artifact sources affecting a pressure sensor as described above. Methods described herein allow signal artifact occurring in or near the frequency range of desired physiological signal information to be detected without filtering, averaging or other signal smoothing methods that might normally be used to remove signal artifact. Artifact removal methods may also remove desired signal information, potentially reducing the sensitivity and specificity of a patient monitoring protocol relying on the sensor signal. As such, the methods described herein rely on detecting the presence of artifact and then making decisions in response to detecting the presence of artifact without attempting to remove the artifact from the signal in order to retain the portion of the signal containing artifact. Decisions made in response to detecting artifact relate to how to use the signal or other actions, e.g. discarding or retaining a signal waveform or entire series of signal waveforms for use in patient monitoring or repositioning the implanted location of the sensor.

FIG. 1 is a schematic diagram of a patient monitoring system including an implantable medical device (IMD) 10 coupled to a lead 14 positioned within a heart 8 in a patient's body 6. IMD 10 is at least capable of monitoring physiological signals and may or may not include therapy delivery capabilities. IMD 10 may correspond to a variety of implantable medical devices including a cardiac pacemaker, implantable cardioverter defibrillator, implantable hemodynamic monitor, a drug pump, a neurostimulator or the like. Accordingly, IMD 10 may be coupled to additional leads and/or catheters operatively positioned relative to the patient's heart 8 or other body tissues for deploying stimulating/sensing electrodes, other physiological sensors, and/or drug delivery ports. While lead 14 is shown terminated within the right ventricle of the patient's heart, it is recognized that lead 14 may be configured as a transvenous lead that extends into other heart chambers or a vein or artery for positioning a pressure sensor in a desired location. Other illustrative locations for a pressure sensor used to monitor a patient include the pulmonary artery, the vena cava, the right atrium, peripheral arteries, larger central arterial locations (such as the aorta) or other locations in the heart or circulation that might not be directly accessed transvenously.

In one embodiment, IMD 10 corresponds to an implantable hemodynamic monitor capable of sensing and recording intracardiac EGM signals and intracardiac pressure signals and storing cardiac electrical and hemodynamic data. EGM signals are sensed using one or more electrodes 18 carried by lead 14 or using alternative electrodes (not shown) incorporated on the hermetically-sealed housing 12 of IMD 10. Housing 12 encloses circuitry (not shown) included in IMD 10 for controlling and performing device functions and processing sensed signals.

Lead 14 includes a pressure sensor 16. Pressure sensor 16 is used for monitoring pressure within the right ventricle. Pressure signals are monitored for determining metrics of hemodynamic function useful in monitoring heart failure status, diagnosing cardiac dysfunction, and other conditions. In embodiments described herein, the right ventricular intracardiac pressure signal obtained from sensor 16 is used to derive one or more hemodynamic variables used to monitor patient condition.

IMD 10 is capable of bidirectional communication with an external programmer 26 via telemetry link 28. Programmer 26 is used to program the operating mode and various operational parameters of IMD 10 as well as interrogate IMD 10 to retrieve data stored by IMD 10. Stored data may include data related to IMD function determined through automated self-diagnostic tests as well as physiological data acquired by IMD 10 using pressure sensor 16 and electrodes 18.

Programmer 26 is further shown in communication with a central database 24 via communication link 30, which may be a wireless or hardwired link. Programming data and interrogation data may be transmitted via link 30. Central database 24 may be a centralized computer or an Internet-based or other networked database used by a clinician for remote monitoring and management of patient 6. Various methods described herein and executed for detecting signal artifact and monitoring pressure variables may be implemented in one or more of the IMD system components shown in FIG. 1, namely in the IMD 10, programmer 26 and/or central database 24, and may include any combination of hardware, firmware and/or software. Programmer 26 may be embodied as a clinic-based programmer having full IMD programming and interrogation functionality or a home-based monitor having interrogation and perhaps limited programming functionality and used for remote patient monitoring. It is recognized that other external devices, such as other physiological monitoring devices or other types of programming devices, may be used in conjunction with IMD 10 and incorporate portions of the methods described herein.

In other embodiments, a pressure sensor may be incorporated within the housing of an IMD, which may be a leadless device including a processor and telemetry circuitry. Such an IMD configured as a leadless sensor is capable of acquiring a pressure signal and transmitting pressure data to another IMD or directly to an external device.

Figure 2:
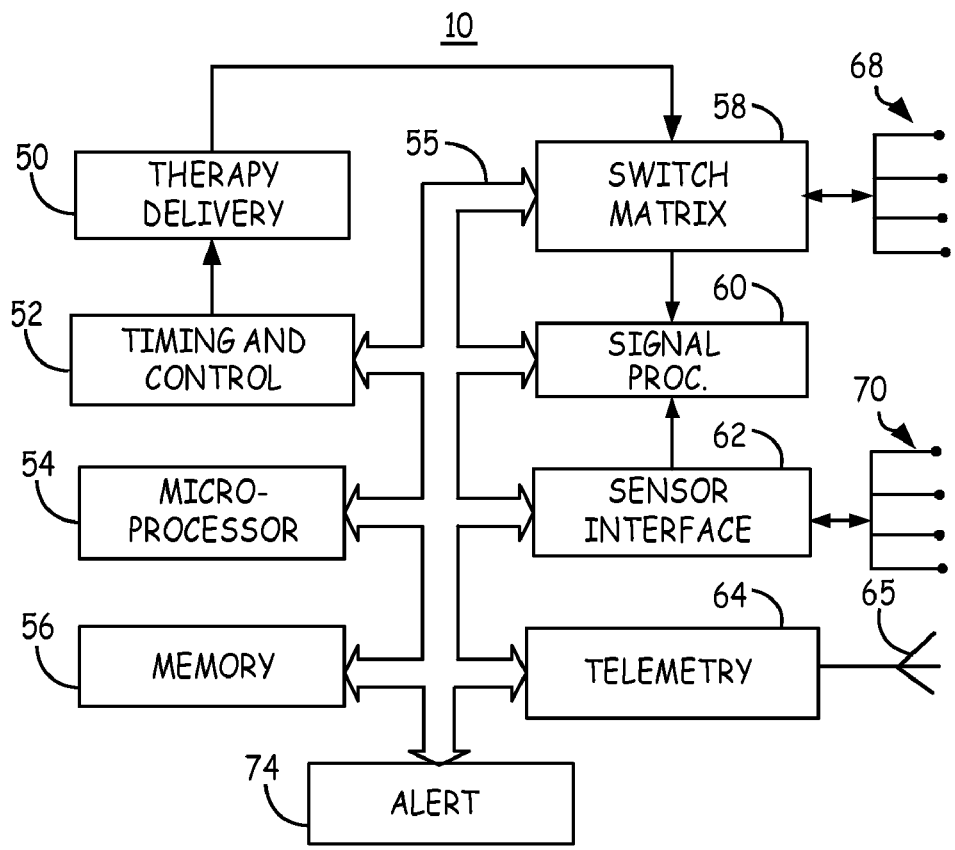
FIG. 2 is a functional block diagram of one embodiment of the IMD shown in FIG. 1.

FIG. 2 is a functional block diagram of one embodiment of IMD 10. IMD 10 generally includes timing and control circuitry 52 and an operating system that may employ microprocessor 54 or a digital state machine for timing sensing and therapy delivery functions (when present) in accordance with a programmed operating mode. Microprocessor 54 and associated memory 56 are coupled to the various components of IMD 10 via a data/address bus 55.

IMD 10 may include therapy delivery module 50 for delivering a therapy in response to determining a need for therapy, e.g., based on sensed physiological signals. Therapy delivery module 50 may provide drug delivery therapies or electrical stimulation therapies, such as cardiac pacing or anti-arrhythmia therapies. Therapies are delivered by module 50 under the control of timing and control circuitry 52.

Therapy delivery module 50 may be coupled to two or more electrode terminals 68 via an optional switch matrix 58 for delivering an electrical stimulation therapy such as cardiac pacing or neurostimulation. Terminals 68 may be coupled to connectors providing electrical connection to electrodes incorporated in IMD housing 12 or other lead-based electrodes, including electrodes 18 carried by lead 14 (shown in FIG. 1).

Electrode terminals 68 may also used for receiving cardiac electrical signals through any unipolar or bipolar sensing configuration. Cardiac electrical signals may be monitored for use in diagnosing or managing a patient condition or may be used for determining when a therapy is needed and controlling the timing and delivery of the therapy. Signal processor 60 receives cardiac signals and includes sense amplifiers and may include other signal conditioning circuitry and an analog-to-digital converter. Cardiac electrical signals received from terminals 68, which may be intracardiac EGM signals, far field EGM signals, or subcutaneous ECG signals, may be used to separate pressure pulse waveforms beat-by-beat in a continuously sensed pressure signal.

IMD 10 is additionally coupled to one or more sensors of physiological signals via sensor terminals 70. Physiological sensors include a pressure sensor 16 as shown in FIG. 1 and may further include other physiological sensors. Physiological sensors may be carried by leads extending from IMD 10, contained inside the IMD (e.g. accelerometers to measure activity levels and/or body position), or incorporated in or on the IMD housing 12.

Signals received at sensor terminals 70 are received by a sensor interface 62 which provides sensor signals to signal processing circuitry 60. Sensor interface 62 receives the sensor signal and may provide initial amplification, filtering, rectification, or other signal conditioning. Sensor signals are used by microprocessor 54 for detecting physiological events or conditions. In particular, signals from pressure sensor 16 are processed by signal processor 60 and/or microprocessor 54 for detecting signal artifact and separating pressure pulse waveforms in which artifact is detected from waveforms in which artifact is not detected. An artifact detection algorithm may be stored in memory 56 and executed by microprocessor 54 with input received from sensor terminals 70. In one embodiment, microprocessor 54 is configured to execute a software-implemented artifact detection algorithm. Artifact detection is performed to discriminate between artifact-contaminated pressure waveforms that are undesirable for use in patient monitoring from pressure waveforms that can reliably be used for determining patient monitoring metrics. As will be further described below, in some cases pressure waveforms containing artifact may still be useful for determining patient monitoring metrics if the artifact is not significantly affecting pressure monitoring metrics derived from the waveform.

Other physiological signals correlated to activity, motion or body position that may be a potential source of artifact in the pressure signal may be monitored. For example, and activity sensor, an accelerometer used to determine patient posture, an EGM/ECG signal used to determine heart rate, an accelerometer for detecting heart motion, a thoracic impedance or other respiration signal that may include signal content relating to respiration as well as coughing or other respiratory maneuvers, or other physiological signals relating to motion or posture may be analyzed to determine a relationship between these potential sources of pressure signal artifact and the frequency of artifact waveforms detected. Such information may be used in determining when and how pressure signal data is used for patient monitoring or reported to a clinician to indicate the reliability of the data during different patient conditions identified using physiological sensor signal data.

The operating system includes associated memory 56 for storing operating algorithms and control parameter values that are used by microprocessor 54. The memory 56 may also be used for storing data compiled from sensed physiological signals and/or relating to device operating history for telemetry out on receipt of a retrieval or interrogation instruction. Microprocessor 54 may respond to the pressure data by altering a therapy, triggering data storage, enabling other sensors for acquiring physiological data, or triggering alert 74 to generate an alert signal to the patient or a clinician that a serious condition has been detected that may require medical intervention. Data relating to pressure signal processing may be stored in memory 56 for later retrieval.

Pressure artifact detection methods may include generating a notification by alert module 74 to notify the patient or a clinician that pressure waveform artifact has reached a significant level, compromising accurate patient monitoring. A notification may be a perceptible signal, e.g. audible or physical, received by the patient or a message transmitted by the IMD using telemetry circuitry 64 and antenna 65. For example, a notification may be generated during a sensor implantation procedure indicating that the pressure signal includes a high degree of artifact and sensor repositioning is recommended.

Figure 3:
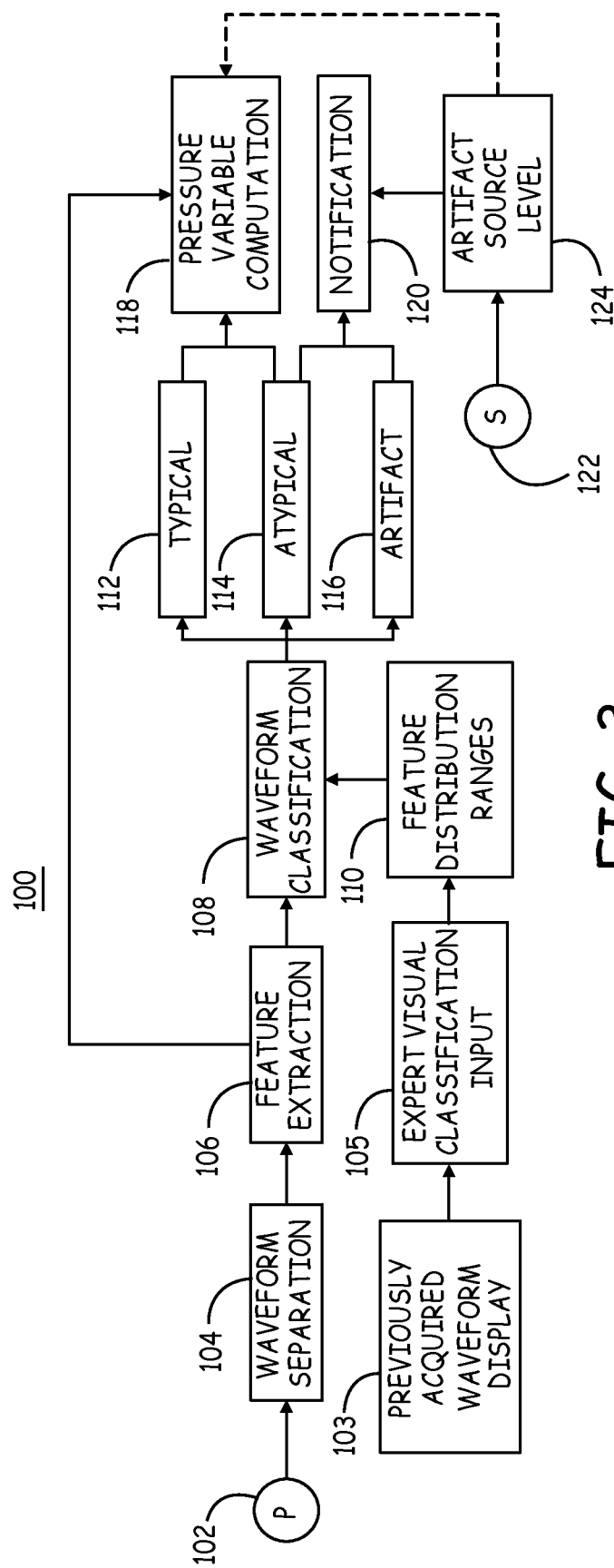
FIG. 3 is a functional block diagram of a method for detecting pressure signal artifact.

FIG. 3 is a functional block diagram of an IMD system configured for detecting pressure signal artifact. A pressure signal 102 sensed by an implantable sensor is received by a processor for pre-processing including waveform separation at block 104. Typically, pressure waveform cycles corresponding to cardiac cycles will be separated or identified to allow features to be extracted from pressure waveforms on a beat-by-beat basis. Waveform separation performed at block 104 includes identifying fiducial points marking the start of each pressure waveform cycle with the end of each cycle corresponding to the start of the next cycle. A fiducial point may correspond to a zero-crossing or other threshold crossing, an inflection point, a local maximum or minimum or other identifiable points. Alternatively, another signal may be used to separate a continuously sensed signal into beat-by-beat waveforms. A cardiac electrical signal sensed using cardiac electrodes may be used in separating pressure signal waveforms based on PP intervals, RR intervals or other EGM/ECG events.

Waveform separation block 102 includes analog-to-digital conversion at a sampling rate that is selected based on desired signal information. Waveform separation block 102 may also include filtering, rectification and other signal conditioning to obtain waveform signals containing the signal information desired for computing patient monitoring metrics. Such signal information may still contain artifact falling in or near the desired signal frequency range.

At block 106, features are extracted from each pressure waveform. Generally multiple features will be extracted from each waveform to provide greater confidence in the artifact detection results. As will be described herein, the features extracted at block 106 may be features that have physiological significance and are used in computing pressure-derived metrics for monitoring the patient condition. Alternatively, the features extracted at block 106 may be features that are not physiologically meaningful but are useful in detecting artifact present in the waveform. In this case, non-physiological features of the waveform extracted at block 106 are not used to compute a pressure-derived monitoring metric but are only used in determining if the waveform is contaminated by artifact in which case it may be rejected when computing a pressure-derived metric for monitoring the patient condition.

The extracted features are used for waveform classification at block 108. In one embodiment, waveforms are classified as typical waveforms 112, atypical waveforms 114 and artifact waveforms 116. Typical waveforms 112 are determined to be free of artifact based on no detection of artifact according to artifact detection rules. Typical waveforms 112 may represent normal or abnormal physiological conditions. Both pathological and non-pathological waveforms are considered to be "physiological" whereas artifact due to sensor motion or other mechanical interference that causes a change in the blood pressure signal without an actual change in blood pressure is considered "non-physiological." Non-physiological artifact may be caused by mechanical contact with nearby anatomical features or sensor motion due to changes in respiration or respiratory maneuvers, changes in cardiac motion or synchrony, for example with the onset of a cardiac pacing therapy, changes in fibrous encapsulation of the sensor, or the like.

Atypical waveforms 114 are determined to include non-physiological artifact but the artifact present is not expected to significantly alter pressure-derived measurements used for monitoring a patient to a degree that would be considered clinically meaningful. Artifact waveforms 116 are waveforms with evidence of non-physiological artifact which would alter pressure-derived monitoring measurements to a clinically significant degree as compared to the same measurement derived from artifact-free (typical) waveforms.

The waveform classification performed at block 108 uses predefined feature ranges, thresholds, or distributions 110 that are defined for the typical, atypical, and/or artifact waveform classifications. The feature distribution ranges 110 are determined for each waveform classification based on expert review of pressure waveforms acquired by the sensing device. As such, previously acquired waveforms are shown on a display 103 to enable an expert to view the waveforms. One or more experts observe and classify the displayed previously obtained pressure waveform recordings as typical, atypical, or artifact waveforms. A user-interface 105 receives the expert classifications. The expert-classified waveforms are then analyzed at processing block 110 to extract waveform features and determine the distribution of the extracted waveform features for each waveform class. This known distribution for each waveform class, based on expert visual observation of previously acquired pressure waveforms, is then used to set rules for classifying unknown waveforms.

The rules are stored in memory of an IMD system so that they can be applied during monitoring of unknown waveforms. The classification of waveforms based on expert observation and determining of waveform feature distributions need only be performed as an initial process and once the distributions are established and rules defined, expert observation is no longer needed to perform automated pressure waveform classification by the IMD system during patient monitoring.

Once the unknown waveforms are classified at block 108, the typical waveforms 112 and atypical waveforms 114 are provided as input to block 118 for use in computing pressure-derived monitoring metrics. The metrics are derived from the pressure signal and monitored over time for detecting a patient condition for diagnostic, prognostic and/or therapy management purposes. If features extracted at block 106 include pressure variables that are physiologically meaningful, those features may be provided as input to block 118 for use in computing the metrics for monitoring a patient's physiological or pathological condition. In some embodiments, artifact waveforms may also be provided as input to block 118 and used for computing monitoring metrics. The percentage of artifact waveforms used in computing a monitoring metric may be determined and logged with the monitoring metric data to establish a confidence level in the computed metric.

Information relating to the frequency of atypical waveforms 114 and artifact waveforms 116 may be used in generating a notification at block 120 to inform the clinician that artifact may be affecting sensor performance. As will be further described below, a high frequency of atypical waveforms 114 and/or artifact waveforms 116 identified during a sensor implantation procedure may generate a notification 120 to alert the clinician that repositioning of the sensor is recommended. A high frequency of artifact waveforms 116 identified after sensor implantation, during patient monitoring, may be used to notify the clinician that pressure monitoring may be based on a limited amount of waveform data. A clinician may choose an appropriate course of action, such as continuation of monitoring using limited data or repositioning the sensor, if necessary.

In some embodiments, one or more additional sensor signals 122 may be evaluated to determine an artifact source level at block 124. Other sensor signals 122 may include, but are not limited to, an activity signal, posture signal, heart rate signal, heart motion signal, respiration signal, or any combination thereof. The sensor signals 122 may be evaluated at block 124 to determine an artifact source level. For example, the activity level, posture, heart rate or other sensor signal information may be included with a notification generated by block 120. Such information may be classified as high, medium and low levels of potential artifact, such as high, medium, low activity, or different heart rate ranges. The potential artifact source information allows a clinician to recognize when periods of high artifact frequency are correlated to high levels of activity, a particular patient posture, high heart rate, bouts of coughing or other potential sources of pressure signal artifact. This information may allow a clinician to program the IMD to perform pressure monitoring during some patient conditions and inhibit pressure monitoring during other patient conditions detected using the sensor signal(s) 122 and associated with high artifact frequency.

Additionally or alternatively, the artifact source level 124 may be stored with computed pressure variables at block 118. Storing an indication of potential artifact source levels derived from other sensor signals may allow a clinician to be able to better interpret pressure data and recognize when pressure data may be influenced by patient conditions that may be causing artifact or generally unreliable data.

Figure 4A:
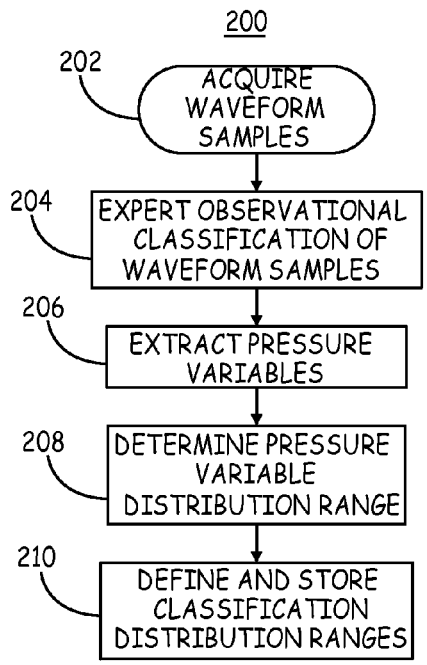
FIG. 4A is a flow chart 200 of one method for detecting pressure waveform artifact.

FIG. 4A is a flow chart 200 of one method for detecting pressure waveform artifact. Flow chart 200, and other flow charts presented herein, are intended to illustrate the functional operation of the implantable medical device system, and should not be construed as reflective of a specific form of software or hardware necessary to practice the methods described. It is believed that the particular form of software will be determined primarily by the particular system architecture employed in the device system. Providing software, hardware and/or firmware to accomplish the described functionality in the context of any modern implantable medical device system, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

The process shown in flow chart 200 is a preliminary process performed to establish the distribution range of extracted features based on expert observation and classification of sample pressure waveforms. This process, therefore, may be performed only once to establish the distribution ranges that will be applied during patient monitoring.

At block 202, pressure waveform samples are acquired using an implantable pressure sensor. Sample waveforms may be acquired from an individual patient or multiple patients. The waveform sampling methods may vary between embodiments and will depend in part on the characteristics of the pressure waveform containing physiological information of interest. Pressure waveforms may be separated into beat-by-beat waveforms using timing markers identified as fiducial points on the pressure waveforms themselves or using other timing markers, such as intracardiac electrogram (EGM) signals. The waveforms are observed by one or more expert observers at block 204 who classify the waveform samples into at least two distinct classes, including an artifact class. In one embodiment, three classifications are made: typical, atypical, or artifact as described above.

An expert can often recognize a waveform as a typical, atypical or artifact waveform quickly through visual observation, without relying on computed or objectively measured values of waveform features. Since overlap of computed or measured values of waveform features between the three categories of waveforms can occur, fully automated methods may not be able to separate typical, atypical and artifact waveforms based only on computed or measured waveform features. As such, expert observation is used initially for classifying acquired waveforms to establish classification criteria to be used by an IMD system during patient monitoring to separate the typical, atypical and artifact waveforms. As will be further described below, once classification criteria are established using expert observation, monitoring methods use the established criteria for classifying pressure waveforms, without requiring further input from an expert.

After acquired waveforms have been classified by observation, pressure variables are extracted at block 206. These pressure variables are clinically meaningful variables that will be used as patient monitoring metrics or used in computing monitoring metrics. The pressure variables that are extracted may vary between applications, depending on the condition(s) being monitored. Pressure variables may include, for example, systolic and diastolic pressures, pulse pressure, zero-crossing points, areas of the pressure waveform, time intervals between fiducial points on the pressure waveform or intervals defined using timing markers obtained from other signals such as EGM. Extraction of pressure variables may also include determining derivatives of the waveform, which may be first, second, third or higher order derivatives. For example a maximum rate of change, +dP/dt max, may be determined from a first derivative of the pressure waveform as one of the extracted features.

In one embodiment, the pressure waveform is an intraventricular pressure waveform. In the Table I, a number of variables are listed, without limitation, which may be extracted from the pressure waveform. Any or all of the listed variables may be extracted at block 206 for use establishing the distribution of these variables in the expert classified waveform samples. Illustrative definitions for the listed variables are provided in Table I, e.g. with specific time windows within which a variable is measured. Other definitions may be conceived for defining clinically meaningful variables derived from the pressure waveform.

When the pressure waveform is measured in other intravascular locations, such as the pulmonary artery, a similar set of pressure variables may be extracted though the definitions of the variables may vary depending on the waveform from which the variable is being extracted. Furthermore, it is recognized that many different pressure variables may be of interest for patient monitoring purposes. The variables of interest may differ between pressure monitoring sites. The examples described herein, therefore, are illustrative and not intended to be an exhaustive list of possible pressure variables that may be of interest or are clinically meaningful in a particular monitoring application.

Other indices or patient monitoring metrics may be computed using extracted pressure variables listed in TABLE I, such as a Myocardial Performance Index (MPI) which may be defined as the ratio (PEI*2)/(STI-PEI) or an RV Function Index, which may be defined as the difference between the RV PP and ePAD. Numerous hemodynamic or cardiac performance metrics or indices may be derived from the pressure signal and will be defined according to a particular monitoring protocol.

TABLE I

| VARIABLE | DEFINITION |
| --- | --- |
| Pre-ejection Interval (PEI) | Time interval measured from a ventricular event (sensed or paced) to $dP/dt_{max}$ occurring within a 200 ms window starting at the ventricular event |
| Systolic Time Interval (STI) | Time interval measured from ventricular event to $dP/dt_{min}$ in a window starting 100 ms after the ventricular event and ending 500 ms later |
| Diastolic Pressure (DP) | Pressure at a ventricular event |
| Systolic Pressure (SP) | Pressure waveform amplitude at the maximum positive peak |
| Pulse Pressure (PP) | Difference between systolic pressure and diastolic pressure |
| Minimum Diastolic Pressure (MDP) | Pressure waveform amplitude measured as the minimum pressure peak during the cardiac cycle |
| Peak-to-Peak Pressure (PPP) | Difference between maximum and minimum pressure waveform peaks |
| Estimated Pulmonary Artery Diastolic Pressure (ePAD) | Pressure at the time of $dP/dt_{max}$ |
| Maximum rate of pressure change ($dP/dt_{max}$) | Maximum amplitude of pressure waveform first derivative occurring within a 200 ms window starting at the ventricular event |
| Minimum rate of pressure change ($dP/dt_{min}$) | Minimum amplitude of pressure waveform first derivative occurring within a window starting 100 ms after a ventricular event and ending 500 ms later |

TABLE I-continued

| VARIABLE | DEFINITION |
| --- | --- |
| Ejection duration (ED) | STI – PEI |
| Ejection duration to RR interval ratio (EDRR) | ED/RR |
| Maximum rate of crossbridge formation (P'P') | $(dP/dt_{max})/(ePAD - DP)$ |
| Time to onset of contraction ($T_{foot}$) | PEI – (ePAD – DP)/ $(dP/dt_{max}/2)$ |
| RV augmentation index (RV AI) | 0.5 * (SP – DP)/(ePAD – DP) |
| Ejection duration (ED) | STI – PEI |

The pressure variables listed in TABLE I are clinically meaningful for the purposes of monitoring the patient's hemodynamic condition and can therefore be used during patient monitoring. Additionally, these variables are used in method 200 for determining distributions of these variables, or any subset thereof, in the expert-classified waveforms.

The variables may be determined on a beat-by-beat basis for each waveform in a series of consecutively recorded waveforms or randomly selected waveforms. At block 208 a distribution of the variables is computed for all of the pressure waveform samples falling into each of the waveform classifications based on expert observation. The distribution may be computed using a stepwise multiple regression analysis to determine if individual variables can be identified as predictors of a waveform classification. However, discrete probabilities for each variable value being in the sample waveforms will have limited predictive value when the probability distributions of the variable for the different waveform classifications have large overlapping regions.

Alternatively, a morphology score for each waveform, $M_j$ is computed using the extracted variable set. For example, an average of the probabilities of each of the variables may be computed as a morphology score as shown by Equation 1:

$$M_j = (\Sigma_{(i=1,n)} Pr(f_i))/n \quad [1]$$

wherein $M_j$ is the morphology score for the $j^{th}$ waveform of a total number (N) of sample waveforms (j=1 ... N) and $Pr(f_i)$ is the discrete probability of the $i^{th}$ extracted variable, $f_i$, (i= 1 ... n) in the samples waveforms.

Figure 5:
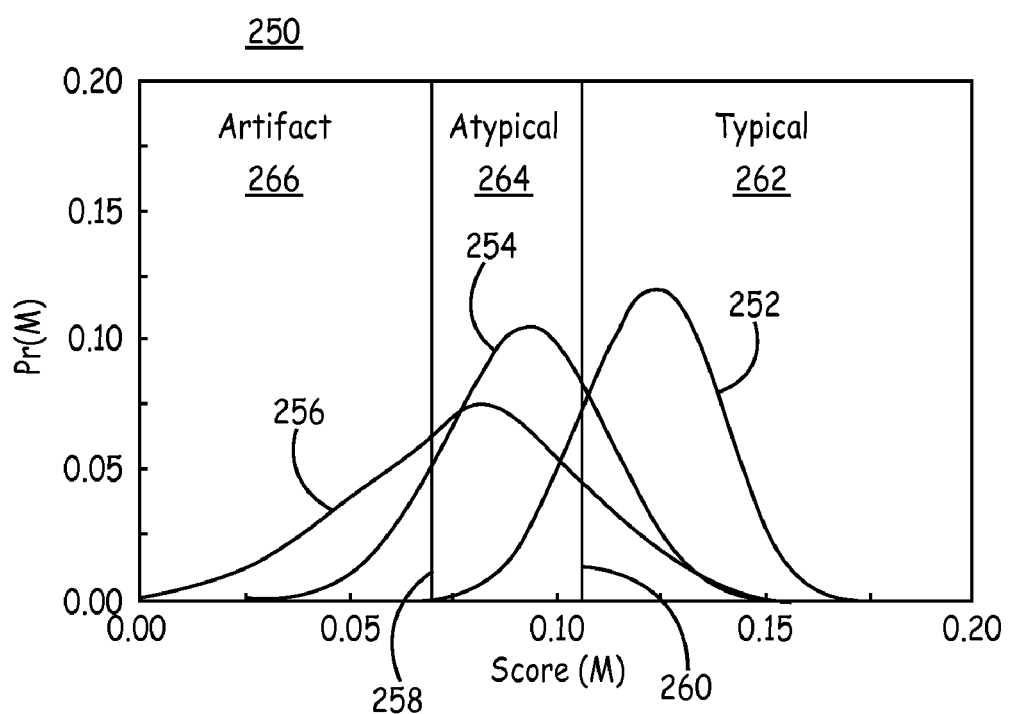
FIG. 5 is a plot of the distribution curves for morphology scores computed using extracted pressure waveform features.

FIG. 5 is a plot 250 of the probability distribution curves for morphology scores computed using extracted features listed in Table I and Equation 1. Randomly selected waveform samples were classified by expert observation. The distributions of the morphology score, Pr(M), computed for typical waveforms 252, atypical waveforms, 254, and artifact 256, are plotted along the y-axis for the range of morphology scores computed for all sample waveforms, shown along the x-axis. Cut-off scores 258 and 260 define morphology score regions 262 (typical), 264 (atypical), and 266 (artifact) that achieve optimal sensitivity and specificity for the morphology score as a discriminator of waveform class.

In this example, overlap between atypical 254 and artifact 252 classes reduces the specificity of the discrimination between these classes. The discrimination between typical 252 and atypical 254 classes and between typical 252 and artifact 256 classes based on the probability distribution of the morphology score yields greater specificity.

The specificity and sensitivity of probability distribution cut-off regions for a morphology score may be further improved through selection and weighting of the probabilities of extracted variables. Providing different weighting to different variables in computing a morphology score may provide further separation of the distribution curves. The waveform class distribution ranges 262, 264 and 266 establish classification criteria that are applied to unknown waveforms to determine which waveforms are physiological and which waveforms are not physiological (i.e. contaminated by artifact). The distribution ranges are unrelated to pathological conditions and thus do not represent thresholds for distinguishing between pathological or non-pathological waveforms or between different severities of a pathological condition.

Referring again to FIG. 4A, the waveform classification ranges are defined at block 210 based on the determined distribution ranges for each waveform class as discussed above in conjunction with FIG. 5. These distribution ranges or thresholds are stored in the IMD for use during patient monitoring for classifying unknown pressure waveforms.

This initial process shown in the flow chart 200 for establishing waveform classification criteria based on expert observation is not necessarily repeated after initially establishing the classification distribution ranges, defined by threshold or cut-off boundaries. Alternatively, process 200 may be repeated periodically to update classification criteria stored by IMD systems performing patient monitoring. The flow chart 200 may be implemented in a personal computer, IMD programmer, Internet-based application or other processor-based device that is configured to display of sample waveforms to a user, receive user-input classification of each of the sample waveforms, and perform statistical analysis of the user-input classifications to determine the distribution of the pressure variables and/or a morphology scored computed from the pressure variables, for each of the waveform classifications. The resulting distribution ranges, i.e. cut-off boundaries or thresholds between waveform classifications, may then be programmed into the memory of an IMD for use by the IMD during patient monitoring.

Figure 4B:
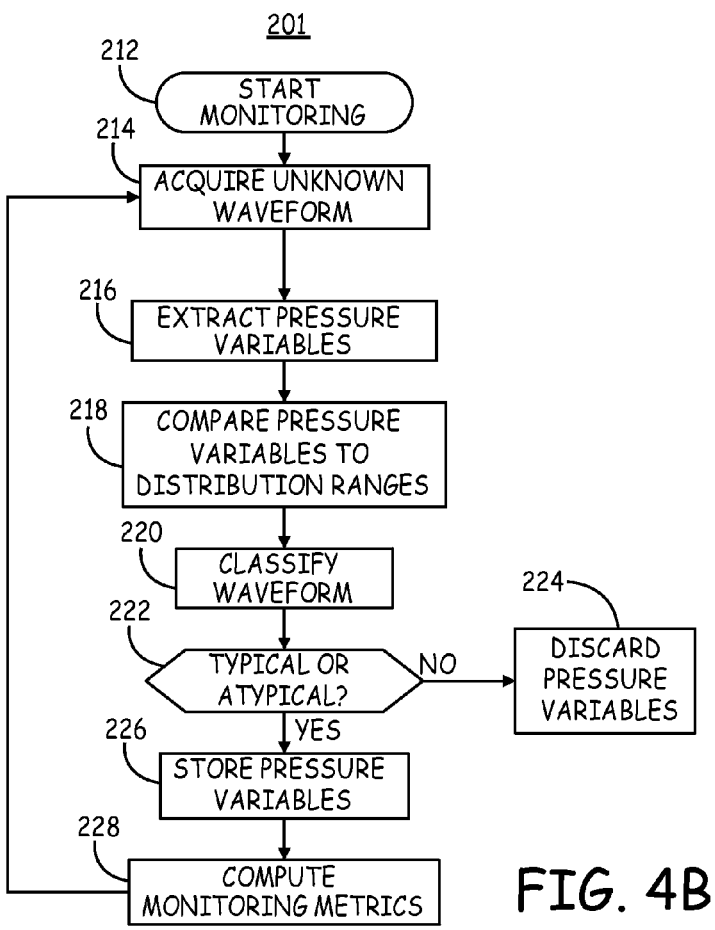
FIG. 4B is a flow chart 201 of a method for performing patient monitoring using the waveform classification criteria established using the process shown in FIG. 4A.

FIG. 4B is a flow chart 201 of a method for performing patient monitoring using the waveform classification criteria established using the process shown in FIG. 4A. Patient monitoring is initiated at block 212. Patient monitoring may be continuous or intermittent depending on the needs for a particular monitoring application. At block 214, unknown pressure waveforms are acquired. Pressure variables to be used for waveform classification are extracted at block 216. These extracted variables correspond to the variables extracted during the process of flow chart 200 (FIG. 4A) and are required for application of the established classification distribution ranges. As discussed above, in this embodiment the extracted variables are variables which are clinically meaningful and serve a dual purposes during patient monitoring in that the pressure variables are used for waveform classification and are additionally used as, or in computing, patient monitoring metrics.

At block 218, the extracted pressure variables are compared to the waveform classification distribution range previously established during process 200 of FIG. 4A and stored in IMD memory. As described above, this comparison may include individual extracted variables or may require computation of a morphology score using multiple extracted variables, which may be combined in linear or non-linear equations. The waveform is classified at block 220 as typical, atypical or artifact according to the distribution range in which the classification variable(s) and/or morphology score falls.

If the waveform is classified as typical or atypical, the pressure variables extracted at block 216 are stored at block 226 and used as, or for computing, patient monitoring metrics at block 228. Since the extracted pressure variables are clinically meaningful variables, the pressure variables themselves may be stored as pressure monitoring metrics. Alternatively, the pressure variables may be used to compute average, maximum, minimum or other statistical features of an extracted variable over multiple pressure waveforms as a monitoring metric. The pressure variables may be used to compute other hemodynamic or cardiac performance metrics.

If the pressure waveform is classified as artifact at block 220, the pressure variables extracted from that waveform are discarded at block 224 and not used for computing patient monitoring metrics. The variables extracted from artifact waveforms are used only for classifying the waveform as artifact, i.e. a non-physiological waveform. The non-physiological waveform is not used for patient monitoring. Physiological waveforms, i.e. those classified as typical and atypical, include clinically meaningful information and will also be used for patient monitoring. The variables extracted from unknown waveforms, therefore, are first used to distinguish between physiological and non-physiological waveforms. The extracted variables from physiological waveforms are further used as monitoring metrics, or for computing monitoring metrics, that can distinguish between pathological and non-pathological conditions or measure the severity of a pathological condition. Details of the patient monitoring methods will vary between applications depending on the condition being monitored.

Alternatively, pressure variables extracted from artifact waveforms may be included when computing patient monitoring metrics at block 228. An indication of the percentage of artifact waveforms included in the computations is stored with the monitoring metrics to establish a confidence level of the metrics.

Figure 6A:
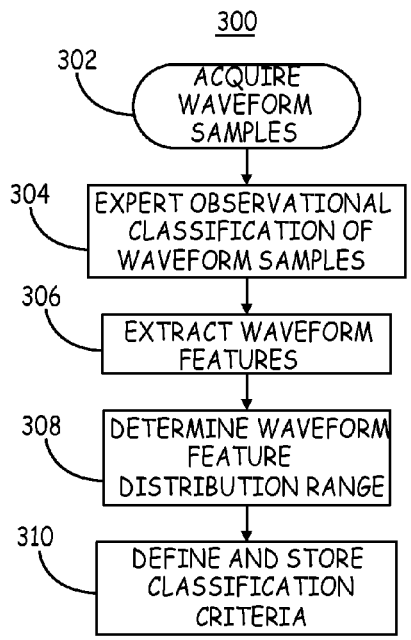
FIG. 6A is a flow chart 300 of an alternative method for establishing waveform classification criteria.

FIG. 6A is a flow chart 300 of an alternative method for establishing waveform classification criteria. The process shown in flow chart 300 is a preliminary process performed with expert input to initially establish the classification criteria which may then be stored in an IMD for use in classifying unknown waveforms during patient monitoring. The process is performed to acquire waveform samples (block 302), classify the waveform samples by expert visual observation (block 304), extract waveform features (block 306), determine feature ranges for each of the waveform classes (block 308), and, based on the feature ranges, define classification criteria (block 310).

In contrast to the feature extraction used in the flow chart 200 shown in FIG. 4A, the waveform features extracted at block 306 include waveform features that are not measured for determining patient monitoring metrics because they are not considered clinically meaningful for determining the status of a pathological condition. Signal artifact commonly appears as a "notch" in the pressure waveform. A "notch" as used herein generally refers to a non-physiological change in waveform amplitude. In one embodiment, features extracted at block 306 relate to detecting and measuring notch features in the pressure waveform. These notches may appear anywhere along the pressure waveform and may therefore be searched for along any segment of the pressure waveform.

Figure 7:
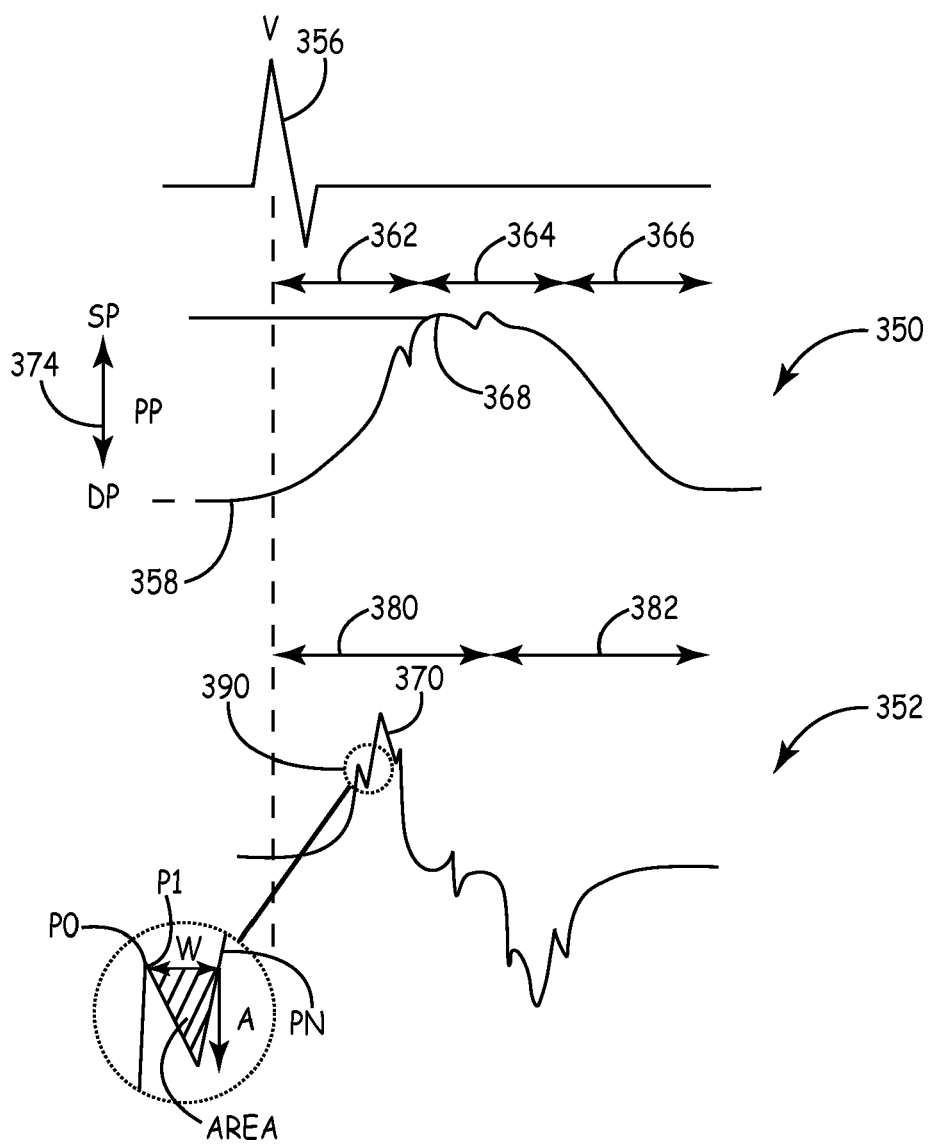
FIG. 7 is a sample pressure waveform and the first time derivative (dP/dt) of the sample waveform.

FIG. 7 is a sample pressure waveform 350 and the first time derivative (dP/dt) 352 of the sample waveform. The pressure waveform and dP/dt waveform can each be divided into segments for searching for the presence of artifact. In one embodiment, the pressure waveform is divided into three segments including an upslope segment 362, a plateau segment 364, and a downslope segment 366. The three segments may be defined using selected reference points identified on the pressure waveform 350 itself, on the dP/dt waveform 352, or on another signal such as a cardiac EGM signal. For example, the upslope segment 362 may be defined to extend from the time of a ventricular electrical event 356, which may be a pacing pulse or an intrinsic depolarization event sensed from a cardiac EGM or subcutaneous ECG signal, until a plateau is detected in the pressure waveform 350. The upslope segment 362 may alternatively be defined relative to the maximum peak +dP/dt 370, including a portion preceding the maximum peak +dP/dt 370 and a portion following the maximum peak +dP/dt 370.

The pressure waveform and any derivatives of the pressure waveform being used are separated into segments that are generally characterized by a substantially consistent increasing or decreasing amplitude trend, i.e. a substantially continuously increasing upslope or continuously decreasing downslope. The plateau segment 364 of the pressure waveform 350 may therefore be subdivided into a beginning plateau portion preceding the systolic pressure 368 (which will be generally increasing) and an ending plateau portion following the peak systolic pressure 368 (which will be generally decreasing).

The maximum peak pressure 368 may be measured as the systolic pressure with the baseline pressure 358 measured as diastolic pressure. The difference between these pressures is measured as the pulse pressure 374.

The dP/dt waveform 352 can be divided into multiple segments including a +dP/dt segment and a −dP/dt segment 382. Each of these segments 380 and 382 may be further divided into upslope and downslope subsegments which are characterized by a generally increasing trend or a generally decreasing trend in amplitude.

Notches are searched for in any selected segments of the pressure waveform 350 or the dP/dt waveform 352 by searching for a reverse in the generally increasing or decreasing trend in amplitude within that segment. Details regarding the identification and measurement of notches will be described further below. Briefly, an example of a notch 390 is shown in the dP/dt waveform 352, shown enlarged in the encircled area. The notch 390 begins at a sample point P1 that is less than the previous sample point P0 indicating a reverse in the general amplitude trend of the +dP/dt upslope segment. The notch 390 ends at a sample point PN that is equal to or greater than the sample point P0. If more than one notch along a segment is detected, the largest notch in each segment may be identified and metrics for the largest notch may be computed as features used to classify the waveform as typical, atypical or artifact. For example the amplitude A, width W and/or area may be computed for the largest notch identified. Alternatively, the number of notches, cumulative sums of notch measurements or other notch metrics may be extracted at block 306 in flowchart 300.

Referring again to FIG. 6A, at block 308, the distribution of the extracted features for each class of the expert-classified waveform samples is analyzed. In particular, thresholds or cut-off values that best distinguish between the waveform classes for the various extracted features are identified. At block 310, classification criteria are defined by identifying the extracted features and corresponding cutoff values or ranges that optimize classification sensitivity and specificity of the waveform samples included in the expert-classified training set. In one embodiment, the classification criteria established at block 310 includes rules that apply thresholds and Boolean logic to the extracted features.

Similar to the process shown in flow chart 200 of FIG. 4A, once the classification criteria are optimized using the expert-classified waveform samples, process 300 need not be repeated. Alternatively, process 300 may be repeated to re-optimize or update the classification criteria, for an individual patient or for a population of patients, that is then programmed into IMD systems performing patient monitoring.

Figure 6B:
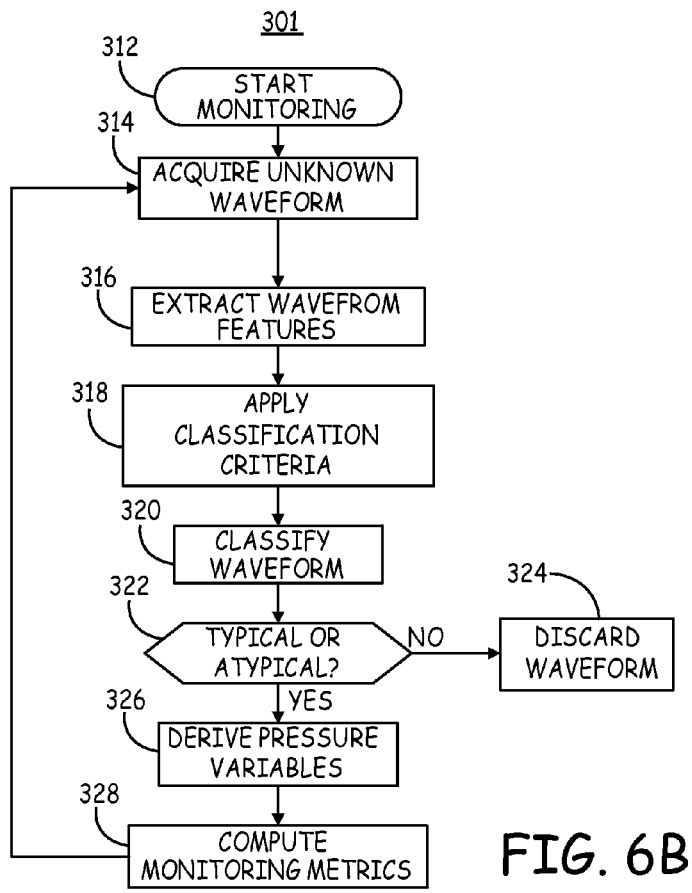
FIG. 6B is a flow chart 301 of a method for performing patient monitoring using the classification criteria established using the process shown in flow chart 300.

FIG. 6B is a flow chart 301 of a method for performing patient monitoring using the classification criteria established using the process shown in flow chart 300. At block 312, patient monitoring is initiated. An unknown waveform is acquired at block 314 and a set of waveform features required for application of the established classification criteria is extracted at block 316. The extracted feature set may be the same as the features extracted during process 300, unless features extracted during process 300 were not included in the optimized classification criteria. One or more features extracted in process 300 may be found to have limited discrimination between waveform classes and therefore not used in the optimized classification criteria.

At block 318, the classification criteria are applied to the extracted features and the waveform is classified accordingly at block 320. If the waveform is typical or atypical, the waveform is further processed to extract desired pressure variables used for patient monitoring at block 326. Since the extracted feature set used to classify the waveform includes features that are not clinically meaningful for the purposes of monitoring a patient condition, pressure variables are derived from the waveform at block 326 for use in computing desired pressure monitoring metrics at block 328.

If the waveform is classified as artifact at block 320, the waveform is discarded at block 324 for patient monitoring purposes. Metrics used for patient monitoring are not computed from pressure variables extracted from the artifact waveform. Alternatively, pressure variables may be extracted from all waveforms, including artifact waveforms, for use in computing patient monitoring metrics. The percentage of artifact waveforms (and optionally atypical waveforms) detected may be stored with the monitoring metrics to establish the confidence level of the computed metrics.

Figure 8:
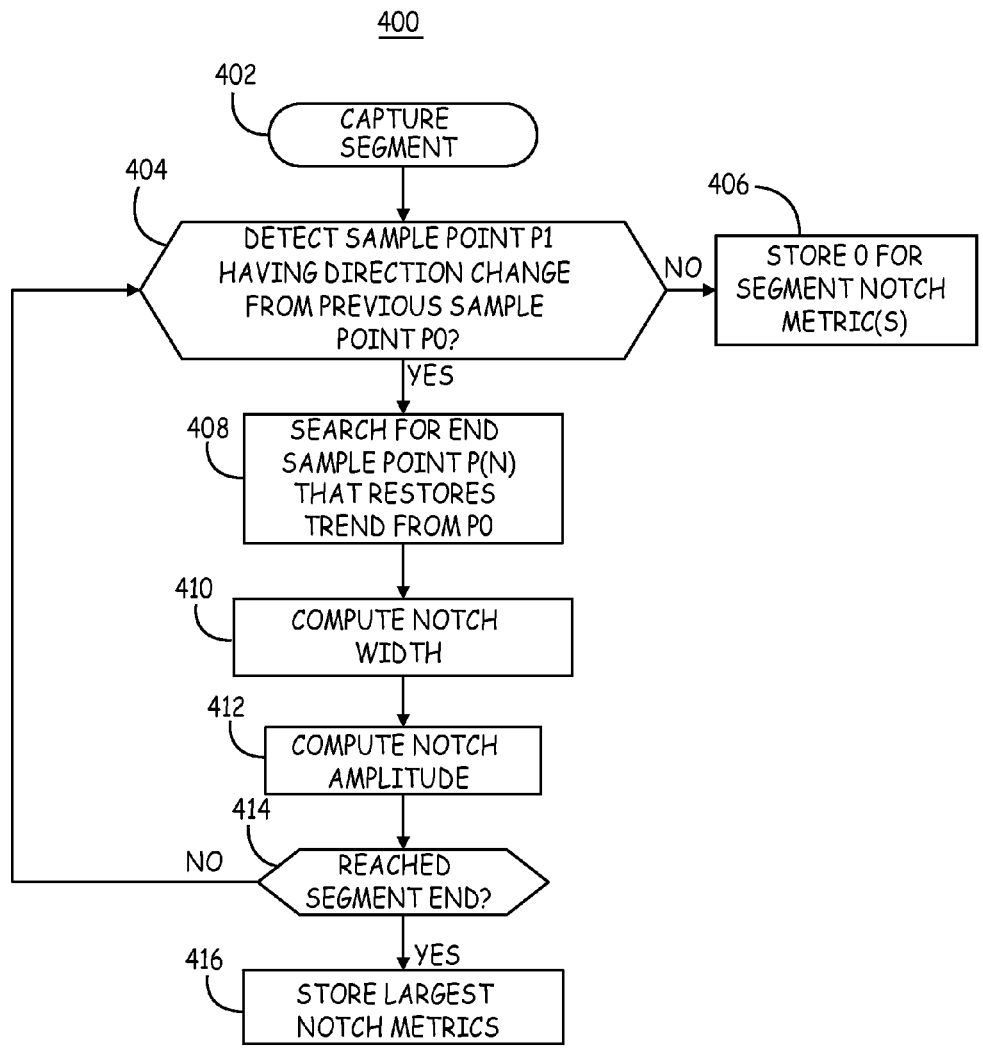
FIG. 8 is a flow chart of a method for extracting features for use in detecting pressure waveform artifact.

FIG. 8 is a flow chart 400 of a method for extracting features for use in detecting pressure waveform artifact. The process shown in FIG. 8 corresponds to the feature extraction that may be performed at blocks 306 and 316 of FIGS. 6A and 6B, respectively. The process relates to searching for a notch in a segment of a pressure waveform, or a derivative of the pressure waveform, and determining a metric of the waveform notch.

At block 402 a segment of a pressure waveform (or a derivative of the waveform) is captured. As described previously, the segment is defined according to reference time points on the waveform itself, on a derivative of the waveform, or another sensed signal. A search for a notch present in the segment is performed by detecting a sample point (P1) that represents a change in the direction of the amplitude trend (increasing or decreasing) of the selected segment. For example, in a segment that generally corresponds to an upslope of the waveform, a sample point P1 that is lower in amplitude than a previous sample point P0 is detected at block 404. If the segment is a downslope portion of the waveform, a sample point P1 that is greater in amplitude than the previous sample point P0 is detected. The previous sample point P0 may be the immediately preceding sample point or a defined number of sample points earlier than the current sample point. If no change in direction in the segment is detected at block 404, the notch metric(s) for that segment are stored as having a zero value at block 406.

If a change in direction is detected at block 404, the point P1 representing the first sample point exhibiting a direction change in amplitude is identified as the start of a notch. At block 408, a search for the end sample point P(N) of the notch is performed. The end sample point is identified as the earliest sample point after P1 that is equal to or crosses the amplitude of the sample point P0. If the segment is an upslope, the endpoint P(N) is the earliest sample point after P1 that has an amplitude equal to or greater than P0. If the segment is a downslope, the endpoint P(N) is the earliest sample point after P1 that has an amplitude equal to or less than P0.

After identifying the start point (P1) and the endpoint P(N) of the notch, various notch metrics may be computed. At block 410, a notch width is computed as the time interval (or number sampling intervals) between the start point P1 and the endpoint P(N). Other notch metrics may be computed such as the notch amplitude at block 410. The notch amplitude may be computed as the differential amplitude between the lowest amplitude sample point and the highest amplitude sample point occurring between (and including) P1 and P(N). Other notch metrics that may be computed may include a notch area and notch slope.

The process represented by flowchart 400 returns to block 404 to continue searching for additional notches until the end of the segment has been reached, as determined at block 414. If the end of the segment has been reached and more than one notch has been detected, notch metrics measured from the largest notch detected are stored at block 416 as extracted features for the waveform being analyzed. The "largest" notch may be selected as the notch having the greatest area in one embodiment. Alternatively, a "largest" notch may be defined as the widest notch or the notch having the highest notch amplitude. Alternatively, a largest notch width, largest notch amplitude, and/or other largest notch metrics for a given segment, but not necessarily measured from the same notch within that segment, may be stored as notch metrics for that segment.

Examples of waveform features that may be extracted from a pressure waveform and the first derivative of the pressure waveform in one embodiment are listed in Table II. Features found to have discriminatory capability, other than notches, may also be used. It is recognized that any combination of the listed features or variations thereof may be used.

TABLE II

| FEATURE | DEFINITION |
|---|---|
| P1 AMP | Amplitude of largest notch on waveform upslope segment |
| P2 AMP | Amplitude of largest notch on waveform plateau segment |
| P2 AREA | Area of largest notch on waveform plateau segment |
| P SYS SLOPE | Sum of the waveform slope from systolic peak pressure in a forward direction and the waveform slope from the systolic peak pressure in a reverse direction |
| PP | Pulse pressure (systolic-diastolic) |
| DPDT1 AMP | Amplitude of largest notch on first +dP/dt upslope segment |
| DPDT2 AMP | Amplitude of largest notch on first +dP/dt downslope segment |
| DPDT2 AREA | Area of largest notch on +dP/dt downslope segment |
| DPDT2 INT | Time interval from maximum +dP/dt to largest notch on +dP/dt downslope segment |
| DPDT3 ZCA | Peak-to-peak amplitude between maximum +dP/dt and minimum -dP/dt |
| DPDT4 AMP | -dP/dt notch amplitude before minimum -dP/dt (downslope subsegment of the -dP/dt segment) as a percent of minimum dP/dt |
| DPDT4 AREA | dP/dt notch area on downslope before minimum dP/dt |
| DPDT5 AMP | dP/dt notch amplitude after minimum dP/dt |
| EDRR | Ejection duration computed as the time interval between the maximum +dP/dt and minimum -dP/dt normalized by the previous RR interval |

As can be seen in Table II, extracted features may include time intervals and other waveform features in addition to notch features. For example, slopes, peak-to-peak differences, and time intervals between features may be extracted. Furthermore, these measures may require using reference time points or intervals obtained from other sensed signals. For example, EDRR in Table II involves measuring an RR interval from an EGM signal for normalizing the ejection duration measured as the time interval between the +dP/dt maximum peak and the -dP/dt minimum peak.

It is recognized that numerous features other than the illustrative examples provided herein may be extracted from a waveform, first time derivative of the waveform, and/or higher order derivatives of the waveform for use in detecting artifact. By examining the distribution of the extracted feature values for each of the sample waveform classes based on expert observations, features that exhibit the greatest separation of the three classes can be selected for establishing waveform classification criteria.

Figure 9:
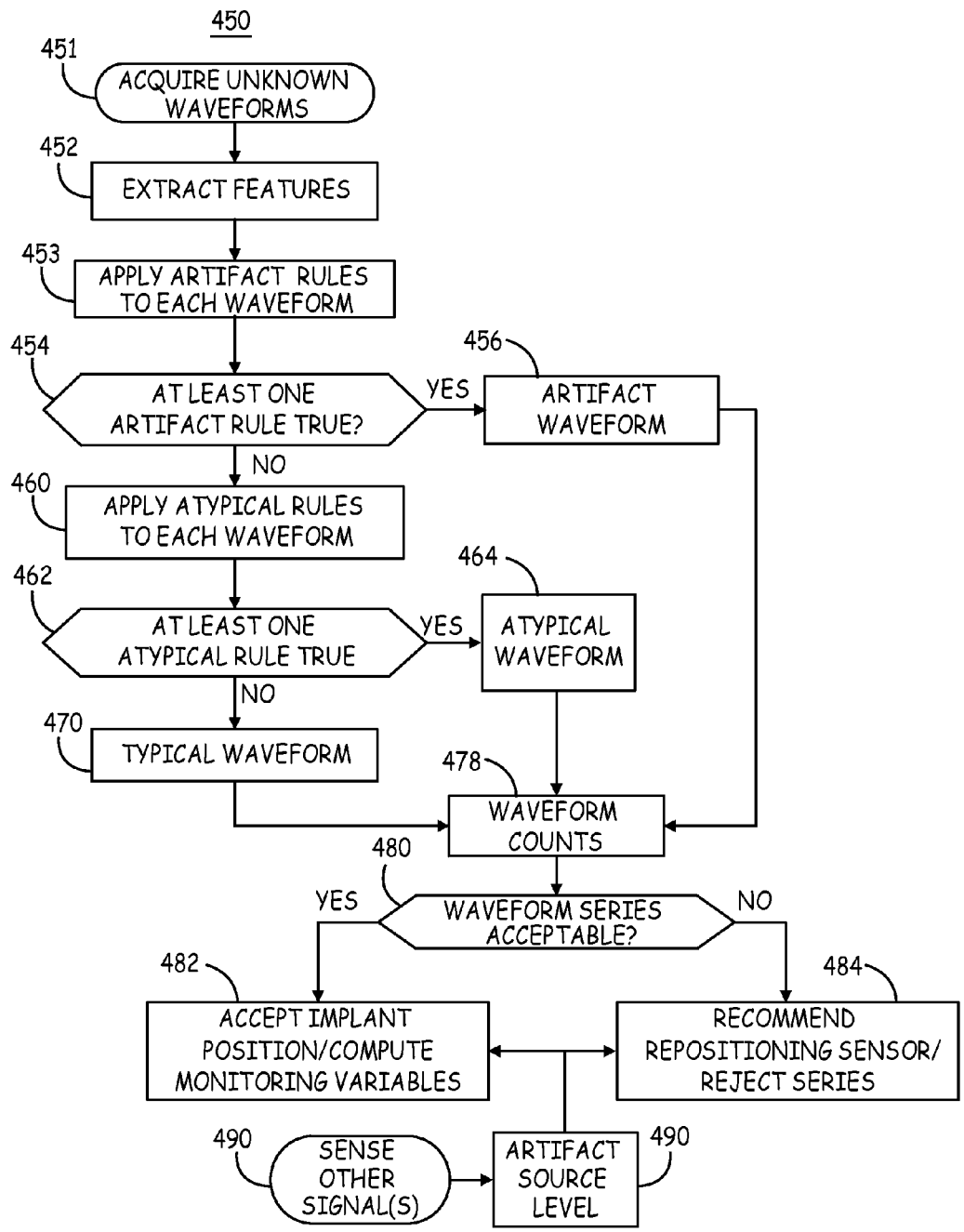
FIG. 9 is a flowchart providing more details of a method for classifying pressure waveforms during pressure sensor implantation and patient monitoring using established classification criteria.

FIG. 9 is a flowchart 450 providing additional details of a method for detecting signal artifact during pressure sensor implantation or during patient monitoring post-implant. In the method shown in flowchart 450, individual waveforms are initially classified according to waveform classification rules then a series of classified waveforms are evaluated based on the frequency of artifact waveforms present in the series. During initial implant, a series of waveforms may be evaluated to guide sensor positioning or set monitoring parameters. During patient monitoring post-implant, a series of waveforms may be evaluated to either reject or establish a confidence level of data obtained from the series of waveforms or to monitor sensor performance.

At block 451, unknown pressure waveforms are acquired using an implanted pressure sensor. At block 452, waveform features are extracted as generally described above. Blocks 453 through 470 represent operations and decisions performed to classify a single waveform and may correspond to the operations performed in blocks 318 and 320 of FIG. 6B. Generally, classification rules are applied to the extracted features for a given waveform in order to classify that waveform. In one embodiment, two sets of rules are applied to extracted waveform features. One set of rules applied at block 453 tests for artifact waveforms and the other set of rules applied at block 460 tests for atypical waveforms. It is recognized that a third set of rules testing for typical waveforms may be applied additionally or alternatively to the atypical waveform rule set and the artifact rule set.

Rules applied at block 453 and 460 may be defined using any of the extracted features. Optimization of waveform classification may be performed to minimize the number of extracted features and applied rules required to achieve an acceptable sensitivity and specificity of waveform classification. Various examples of Boolean logic-based rules defined using extracted features and thresholds are listed in Table III While specific rules are listed for illustrative purposes, it is recognized that numerous rule definitions may be conceived which combine Boolean operators and threshold comparisons applied to values of extracted features. An optimal rule set can be defined for a particular sensor and monitoring application by determining rules and thresholds that provide the greatest sensitivity and specificity for discriminating between waveform types. The term "thresh" used in Table III refers generally to a threshold selected for the particular feature and discrimination rule in which it appears. While the term "thresh" is used commonly in each of the example rules listed in Table III, it is not intended to suggest that the same threshold value is used for the various features and rules. It is to be understood that a unique and optimal threshold value is determined for each feature and discrimination rule for a given sensor and monitoring application.

TABLE III

| 1 | DPDT1 ≧ thresh |
|---|---|
| 2 | (P SYS SLOPE ≧ thresh) AND (HR MEAN < max) |
| 3 | {(DPDT3 AREA ≧ thresh1) AND (DPDT3 amp ≧ thresh)} OR (DPDT3 AREA ≧ thresh2*) *thresh2 ≧ thresh1 |
| 4 | {(DPDT2 AMP ≧ thresh) AND (DPDT2 AREA ≧ thresh1) AND (DPDT2 INT ≧ thresh)} OR DPDT2 AREA ≧ thresh2* *thresh2 > thresh1 |
| 5 | (DPDT4 AMP ≧ X % of minimum −DP/DT) AND (DPDT4 AREA ≧ thresh) |

A set of rules for detecting a waveform type may be defined such that if at least one rule is found true (i.e. performing an OR operation between all rules in a rule set), the waveform is classified according to that waveform type. The set of rules may alternatively be defined such that all rules must be true (i.e. performing an AND operation between all rules in a rule set) in order to classify the waveform as that waveform type. Each set of rules may include any combination of rules, such as those listed in TABLE III or any other defined rules which combine Boolean operations and threshold comparisons.

As illustrated by the examples in TABLE III, a single rule within a set of rules may include a single feature threshold comparison or multiple feature threshold comparisons combined using Boolean operators such as AND, OR, or other operators. Rules may include features or measurements derived from other sensor signals, e.g. as in Rule 4 above, which includes a term related to heart rate, HR MEAN, measured from an EGM signal. Thresholds may be defined as fixed values or variable values. A variable threshold may be defined as a function of another waveform feature, e.g. as in Rule 5 above in which a threshold is defined as a percentage of another waveform feature, in this case a percentage of the minimum −dP/dt peak.

At block 453, the artifact rule set is applied to the set of extracted waveform features. If any one of the artifact rules is determined to be true at block 454, the waveform is classified as artifact at block 456. If none of the artifact rules are satisfied, the atypical rule set is applied to the extracted features of each of the unknown waveforms at block 460. An atypical rule set may include rules defined in the same manner as the atypical rules set but using differently defined thresholds. Alternatively, the two rule sets may be entirely unique and distinct from each other.

If any one of the atypical rules is determined to be true at block 462, the waveform is classified as atypical at block 464. If none of the artifact nor atypical rules are satisfied, the waveform is classified as typical at block 470.

The rule set yielding a "worst" case result is thus used as the final waveform classification. In other words, if an artifact rule is determined to be true, the waveform is classified as an artifact waveform at block 466 and this result overrides an atypical classification based on any of the atypical rules being satisfied. If an atypical rule is determined to be true (decision block 462), and none of the artifact rules are true, the waveform is classified as atypical (block 464). If none of the atypical rules and none of the artifact rules are determined to be true, the waveform is classified as typical (block 470).

In some embodiments, the individual waveform classifications may be used for deciding whether to accept or reject an implant location or to accept or reject a waveform for patient monitoring purposes. In other embodiments, the waveform monitoring protocol further requires an evaluation of a series of waveforms to determine if the entire waveform series is acceptable or not. If a high frequency of artifact is found within a series of waveforms, a decision may be made regarding a best course of action. For example, the sensor may be repositioned during an implant procedure or the entire series may be discarded for use in patient monitoring as being contaminated by artifact.

To evaluate an entire series of waveforms for artifact contamination, a counter for the appropriate waveform class is updated at block 478 as each individual waveform is classified. A series of recorded waveforms may include a predetermined or a variable number of waveforms depending on the monitoring protocol, e.g. all of the waveforms identified during a predetermined time interval.

The waveform counts are analyzed at block 480 to determine if the waveform series is acceptable. The individual counts for each waveform class can be compared to each other or compared to a combined count of the total number of waveforms in all three waveform class. For example, if the number of typical waveforms (or total number of typical and atypical waveforms) as a percentage of the combined count exceeds a threshold, the waveform series is acceptable. Conversely, if the number of artifact waveforms (or total number of atypical and artifact waveforms) exceeds a threshold, the series is unacceptable.

If the process shown in flowchart 450 is being performed during an implant procedure and the series is found acceptable, the implant position is determined to be acceptable at block 482. A notification may be transmitted from the IMD or generated by an external programmer in response to receiving data from the IMD to display to the implanting clinician that the implant position is acceptable. If the series is unacceptable, a notification is generated at block 484 indicating that sensor repositioning is recommended due to artifact contamination.

Alternatively, the waveform series evaluation may guide programming of the monitoring mode and/or monitoring parameters based on the frequency of artifact (and/or atypical) waveforms appearing in a series of waveforms. For example, a patient monitoring mode that produces a limited set of monitoring metrics, uses limited pressure data, is enabled during limited time periods, or other monitoring limitations, may be selected which allows patient monitoring to be performed using the current sensor position even though artifact is present.

If the process shown in flowchart 450 is being performed during patient monitoring post implant, and the waveform series is determined acceptable at block 480, the series is accepted for monitoring metric computations at block 482. Individual artifact waveforms within the series may still be rejected for computing monitoring variables, but typical and atypical waveforms may be used to compute patient monitoring metrics. Alternatively, the entire series may be used for computing metrics with an indication of the artifact frequency to establish a metric confidence level. If the series is determined unacceptable, the entire series may be rejected at block 484 for use in patient monitoring purposes due to artifact contamination. If a high number of waveform series become rejected, a warning or alert may be generated to notify the clinician that the sensor may need repositioning or other intervention may be required due a limited amount of acceptable signal data.

In some embodiments, additional sensor signals are sensed during post-implant monitoring at block 490 to provide a clinician with information about possible artifact source levels. For example, high, medium or low activity level, heart rate range, or detected patient posture may be identified at block 490 The potential artifact source level may then be provided as input to blocks 482 and 484 so that artifact source level may be reported with the frequency of detected artifact waveforms, either when monitoring variables are computed at block 482 or when a waveform series is rejected at block 484 or both. The detected artifact may be subclassified as being associated with high activity, a particular posture, a high heart rate, or other potential source of pressure signal artifact. This additional information provides a clinician with valuable insight in interpreting the pressure monitoring variables.

The process shown in flowchart 450 is described with regard to extracted waveform features that include features not used for patient monitoring, e.g. notch features that do not have physiological meaning. It is contemplated that the described rule sets including feature threshold comparisons and Boolean operators may also be defined based only on waveform features that are physiologically meaningful and used for patient monitoring purposes when the waveform series is determined acceptable. Furthermore, the methods described above in conjunction with FIGS. 4A, 4B and 5, which rely on physiologically meaningful variables used for determining a feature distribution and establishing waveform classification criteria, e.g., using a morphology waveform score, may alternatively be used to classify each individual waveform in method 450 before analyzing a series of waveforms at blocks 470 through 484.

Thus, an implantable medical device system and associated method for detecting sensor signal artifact have been presented in the foregoing description with reference to specific embodiments. It is appreciated that various modifications to the referenced embodiments may be made without departing from the scope of the disclosure as set forth in the following claims.

The invention claimed is:

1. A medical device system for monitoring a physiological signal in a patient and detecting artifact in the physiological signal, the system comprising:
an implantable physiological sensor for sensing the physiological signal;
a display for displaying the physiological signal to enable an expert to classify individual waveforms of the physiological signal based on visual observation, the individual waveforms classified into at least two classes comprising an artifact class;
a user interface for receiving user input to establish the classification of each of the individual waveforms;
a memory for storing the user input classifications of the individual waveforms;
a processor configured to:
receive the implantable physiological sensor signal;
separate the signal into a plurality of individual waveforms;
extract a plurality of features from each individual waveform;
determine a distribution range for the plurality of features for each of the classes, and
establish waveform classification criteria in response to the determined distribution ranges; and
an implantable processor adapted to be coupled to an implantable physiological sensor, the implantable processor configured to:
acquire unknown waveforms from the implantable physiological sensor,
extract the plurality of features from the unknown waveforms,
classify the unknown waveforms according to the established waveform classification criteria, and
detect signal artifact in response to a waveform being classified in the artifact class, wherein the at least two classes further comprise an atypical class and a typical class, the implantable processor further configured to:
determine a percentage of the unknown waveforms classified as each of the artifact class, atypical class, and typical class;
compute a monitoring metric using the unknown waveforms; and
report the monitoring metric with the percentage of one of the artifact, atypical and typical classes to establish a confidence level of the reported metric.

2. The system of claim 1 wherein determining the distribution range comprises computing a morphology score as a function of the extracted features and determining the distribution range of the morphology score for each of the classes.

3. The system of claim 1 wherein the implantable processor is further configured to compute a metric for monitoring a physiological condition of the patient, the metric computed as a function of at least one of the features extracted from the unknown waveforms in response to an unknown waveform not being classified in the artifact class.

4. The system of claim 1 wherein the plurality of features extracted comprises a non-physiological feature of the waveform, the non-physiological feature used for classifying the unknown waveforms; and
the implantable processor further configured to extract a physiological feature from an unknown waveform in response to the unknown waveform not being classified in the artifact class, and
compute a metric as a function of the physiological feature for monitoring a physiological condition of a patient.

5. The system of claim 4 wherein the implantable processor is further configured to:
extract a physiological feature from the unknown waveforms classified in the artifact class;
compute the monitoring metric using the physiological feature extracted from unknown waveforms classified in the artifact class and the physiological features extracted from unknown waveforms not classified in the artifact class;
determine a frequency of the unknown waveforms classified in the artifact class; and
store the monitoring metric with the frequency.

6. The system of claim 1 wherein the established criteria comprise a plurality of rules defined for detecting a waveform class, the plurality of rules comprising a threshold comparison established in response to determining the distribution range of an extracted feature and at least one rule of the plurality of rules comprising a Boolean logic operation.

7. The system of claim 6 wherein the threshold comparison comprises comparing a first feature extracted from an unknown waveform to a variable threshold that is dependent on a second feature extracted from the unknown waveform and different than the first feature.

8. The system of claim 1 wherein extracting the plurality of features comprises computing a waveform derivative.

9. The system of claim 1 wherein the implantable processor is further configured to count a number of the unknown waveforms being classified in the artifact class and generate a notification in response to the count.

10. The system of claim 1 further comprising counting a number of the unknown waveforms being classified in the artifact class in a series of waveforms and reject the entire series of waveforms as artifact in response to the count.

11. The system of claim 1 further comprising:
a second physiological signal in the patient for sensing signal correlated to a potential source of artifact in the plurality of unknown waveforms;
the implantable processor further configured to receive the second physiological signal, determine a potential artifact source level from the second physiological signal, determine a frequency of artifact waveform classifications occurring in the unknown waveforms, and store the artifact source level with the frequency of artifact waveform classifications.

12. A medical device system for monitoring a physiological signal in a patient and detecting artifact in the physiological signal, the system comprising:
an implantable physiological sensor for sensing the physiological signal;
a display for displaying the physiological signal to enable an expert to classify individual waveforms of the physiological signal based on visual observation, the individual waveforms classified into at least two classes comprising an artifact class;
a user interface for receiving user input to establish the classification of each of the individual waveforms;
a memory for storing the user input classifications of the individual waveforms;
a processor configured to:
receive the implantable physiological sensor signal;
separate the signal into a plurality of individual waveforms;
extract a plurality of features from each individual waveform;
determine a distribution range for the plurality of features for each of the classes, and
establish waveform classification criteria in response to the determined distribution ranges; and
an implantable processor adapted to be coupled to an implantable physiological sensor, the implantable processor configured to:
acquire unknown waveforms from the implantable physiological sensor,
extract the plurality of features from the unknown waveforms,
classify the unknown waveforms according to the established waveform classification criteria, and
detect signal artifact in response to a waveform being classified in the artifact class, wherein the plurality of features extracted comprises a non-physiological feature of the waveform, the non-physiological feature used for classifying the unknown waveforms; and
the implantable processor further configured to extract a physiological feature from an unknown waveform in response to the unknown waveform not being classified in the artifact class, and
compute a metric as a function of the physiological feature for monitoring a physiological condition of a patient, and wherein the non-physiological feature comprises one of a notch amplitude, a notch width, and a notch area.

13. A medical device system for monitoring a physiological signal in a patient and detecting artifact in the physiological signal, the system comprising:
an implantable physiological sensor for sensing the physiological signal;
a display for displaying the physiological signal to enable an expert to classify individual waveforms of the physiological signal based on visual observation, the individual waveforms classified into at least two classes comprising an artifact class;
a user interface for receiving user input to establish the classification of each of the individual waveforms;
a memory for storing the user input classifications of the individual waveforms;
a processor configured to:
receive the implantable physiological sensor signal;
separate the signal into a plurality of individual waveforms;
extract a plurality of features from each individual waveform;
determine a distribution range for the plurality of features for each of the classes, and
establish waveform classification criteria in response to the determined distribution ranges; and
an implantable processor adapted to be coupled to an implantable physiological sensor, the implantable processor configured to:
acquire unknown waveforms from the implantable physiological sensor,
extract the plurality of features from the unknown waveforms,
classify the unknown waveforms according to the established waveform classification criteria, and
detect signal artifact in response to a waveform being classified in the artifact class, wherein the plurality of features extracted comprises a non-physiological feature of the waveform, the non-physiological feature used for classifying the unknown waveforms; and
the implantable processor further configured to extract a physiological feature from an unknown waveform in response to the unknown waveform not being classified in the artifact class, and
compute a metric as a function of the physiological feature for monitoring a physiological condition of a patient, and wherein extracting the non-physiological feature comprises dividing the waveform into a plurality of segments and searching within one of the plurality of segments for the non-physiological feature.

* * * * *